United States Patent [19]

Memmen

[11] Patent Number: 5,370,607
[45] Date of Patent: Dec. 6, 1994

[54] GLAUCOMA IMPLANT DEVICE AND METHOD FOR IMPLANTING SAME

[75] Inventor: James E. Memmen, Green Bay, Wis.

[73] Assignee: Annuit Coeptis, Inc., Green Bay, Wis.

[21] Appl. No.: 967,442

[22] Filed: Oct. 28, 1992

[51] Int. Cl.$^5$ .................... A61M 5/00; A61M 27/00
[52] U.S. Cl. ............................ 604/8; 604/9; 604/294; 623/4
[58] Field of Search ............... 604/8–10, 604/294; 623/4

[56] References Cited

U.S. PATENT DOCUMENTS

| | | | |
|---|---|---|---|
| 4,037,604 | 7/1977 | Newkirk | 604/9 |
| 4,428,746 | 1/1984 | Mendez | 604/8 |
| 4,457,757 | 7/1984 | Molteno | 604/294 |
| 4,521,210 | 6/1985 | Wong | 604/8 |
| 4,554,918 | 11/1985 | White | 604/10 |
| 4,604,087 | 8/1986 | Joseph | 604/9 |
| 4,722,724 | 2/1988 | Schocket | 604/8 |
| 4,729,761 | 3/1988 | White | 604/8 |
| 4,750,901 | 6/1988 | Molteno | 604/8 |
| 4,787,885 | 11/1988 | Binder | 604/8 |
| 4,826,478 | 5/1989 | Schocket | 604/8 |
| 4,886,488 | 12/1989 | White | 604/9 |
| 4,902,292 | 2/1990 | Joseph | 604/9 X |
| 4,936,825 | 6/1990 | Ungerleider | 604/8 |
| 4,946,436 | 8/1990 | Smith | 604/8 |
| 4,968,296 | 11/1990 | Ritch | 604/8 |
| 5,071,408 | 12/1991 | Ahmed | 604/9 X |
| 5,073,163 | 12/1991 | Lippman | 604/9 |
| 5,171,213 | 12/1992 | Prize, Jr. | 604/9 |
| 5,178,604 | 1/1993 | Baerveldt et al. | 604/8 |

OTHER PUBLICATIONS

Minkler, et al., *Molteno Implant in Complicated Glaucomas*, Opthalmology Clinics of North America, 1: 211–220 (1988).

Krupin, et al., *Posterior Tube Seton Implants*, Opthalmology Clinics of North America, 1: 209–210 (1988).

Krupin, et al., *Krupin–Denver Valve Implant*, Opthalmology Clinics of North America, 1: 221–224 (1988).

Wilson, R. P., *The Shocket Shunt*, Opthalmology Clinics of North America, 1: 225–232 (1988).

Hitchings, R. A., *One Piece Tube and Plate Implant for Glaucoma Drainage Surgery*, Opthalmology Clinics of North America, 1: 233–238 (1988).

Primary Examiner—Randall L. Green
Assistant Examiner—Mary Beth Jones
Attorney, Agent, or Firm—Patula & Associates

[57] ABSTRACT

A pre-assembled, preferably single piece, device and related surgical procedure, to be surgically implanted in an eye for treating refractory glaucoma by draining aqueous out of the anterior chamber using a tubular shunt depended from a flexible band having a main reservoir and at least two wings extended in directions opposite one another away from said main reservoir, said wings each having a neck portion defining a depression in said band and an anchoring head each having a tip end and a lock end, with each said anchoring head gradually increasing in thickness to form a taper from each said tip end to each respective lock end to guide each said anchoring head under and past the extraocular muscles of the eye, which muscles then rest in said depressions locked against each said lock end, said device being further defined by a plurality of circumferential markings regularly placed along said tubular shunt for placement within the anterior chamber according to the size eye of each respective patient, and a ligature integrally formed on the exterior of said main reservoir above said tab to releasably pre-crimp said tubular shunt for restricting aqueous flow immediately after implantation of said device for a sufficient period to prevent hypotony, after which period said ligature can be released to allow for safe flow of aqueous.

36 Claims, 2 Drawing Sheets

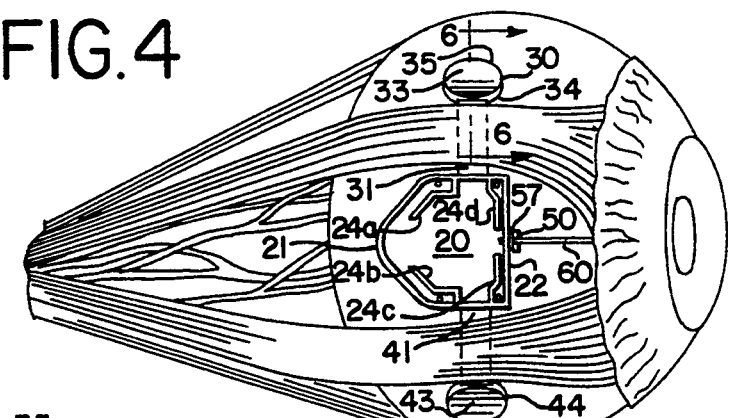
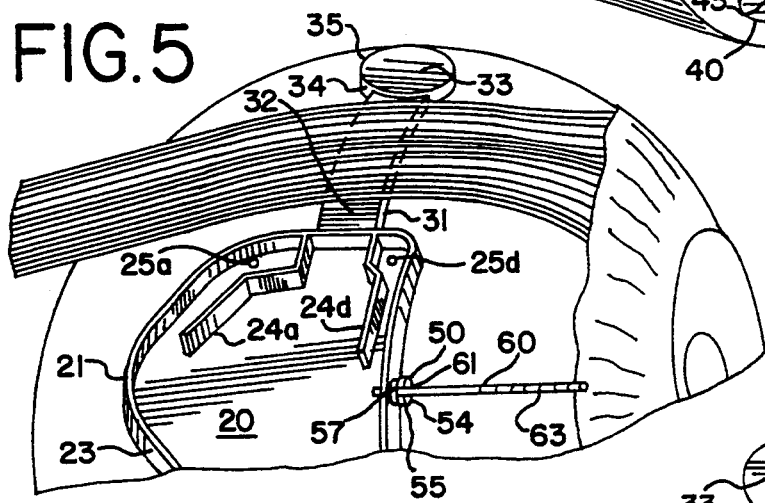
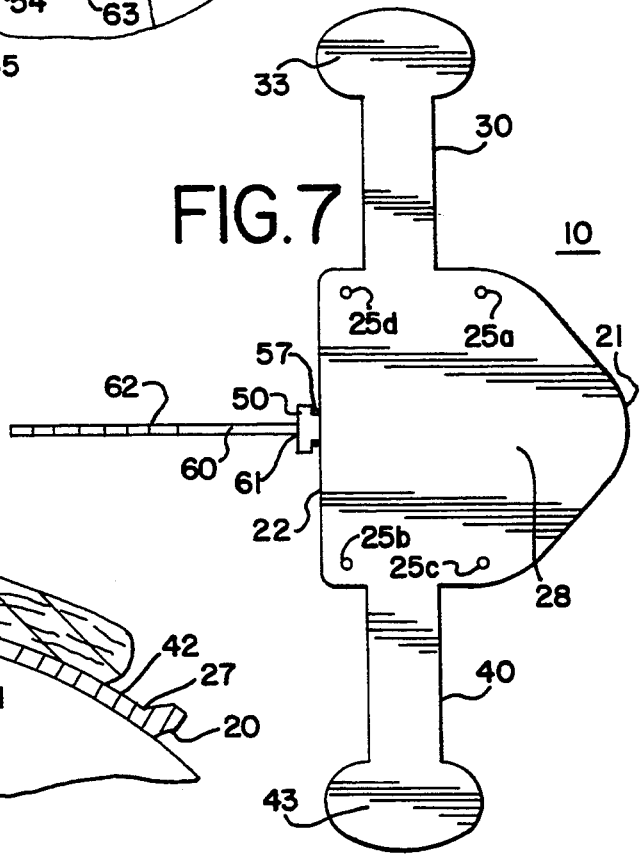
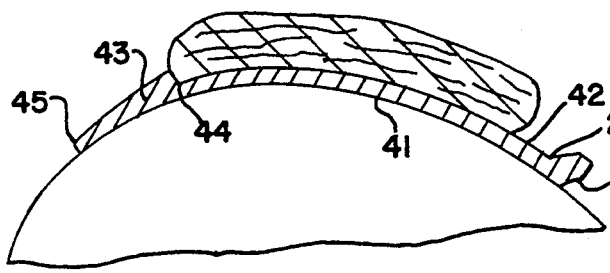

GLAUCOMA IMPLANT DEVICE AND METHOD FOR IMPLANTING SAME

This invention pertains to glaucoma implant devices and related surgical procedures, particularly flexible, pre-assembled implant devices used for treating refractory glaucoma by reducing intraocular pressure through the draining of aqueous humor from the anterior chamber of the eye using a tubular shunt.

BACKGROUND OF THE INVENTION

Glaucoma is a family of diseases of the eye which is characterized by increased intraocular pressure. If left untreated, over time glaucoma causes progressive and irreversible damage to the optic nerve, with associated loss of the midpheripheral vision which then subsequently spreads into the far peripheral vision as well as the central vision. Severe cases of this disease usually result in blindness if adequate control of intraocular pressure is not achieved.

Historically, a variety of approaches have been used to treat glaucoma, namely topical medications, oral medications, lasers and surgical procedures designed to create a fistula for the aqueous humor in the eye to the external surface of the eye. The common goal of all of these modalities is to reduce intraocular pressure and thereby prevent progressive damage. Surgical treatment of glaucoma has a long history pre-dating the twentieth century. The means of surgical treatment have been varied and numerous, although none have succeeded entirely satisfactorily in lowering intraocular pressure, and in minimizing the risks of complications associated with these various procedures which in and of themselves may be vision threatening.

In general, glaucoma is treated surgically only when other treatment measures have failed. Usually surgical treatment involves the creation of a simple fistula by incising an opening in the anterior chamber angle to allow the free flow of aqueous into the subconjunctival space. The procedure is reasonably successful with approximately seventy-five percent of the patients having adequate pressure control for five years. The most frequent cause of failure is external scarring of the opening which occludes the flow of fluid out of the eye and results in a return to a state of increased intraocular pressure.

A second attempt at fistulization may be performed with or without the use of chemical agents which retard external scarring. The chemical inhibitors of scar tissue are usually not used on initial procedures because of an associated risk of increased postoperative complications. The success rate of such second attempts is approximately sixty percent.

Many patients unfortunately still fail multiple standard filtering operations. Intermittently over the last fifty years, the use of a tube or shunting device to transport aqueous farther posteriorly where scarring would be less likely to occur has been attempted in an effort to offer treatment to those who in the past frequently only went blind because of the scarring of the openings made by the standard surgical treatment(s). This class of devices is known as setons.

Setons have been made available in numerous sizes, shapes and configurations. Prior to the advent of microsurgery, these devices often were made of a myriad of materials including metallic substances which frequently eroded into the eye or extruded from the eye and therefore many of these attempts, especially those of the 1950s and 1960s, were abandoned because of unacceptable complications associated with the procedure. Newer glaucoma seton devices have gained in popularity given the markedly improved results they achieve, however, these newer devices still present numerous problems.

Regarding the newer seton devices commercially available, significant complications of surgery which require second operations occur in approximately thirty to thirty-five percent of cases in the immediate perioperative period. Many of these devices are cumbersome, difficult to implant, require multiple procedures as part of the general strategum for implantation or are not premanufactured and require manufacture by the surgeon prior to implantation.

For example, one such newer implant device for the drainage of aqueous humor in the treatment of glaucoma was disclosed by Molteno in U.S. Pat. Nos. 4,750,901 and 4,457,757. According to Molteno, an implant comprised of a rigid circular plate having an upper ridge and a subsidiary ridge is sutured to the sclera of an eye. A tube connected to the implant is passed through the sclera to the anterior chamber of the eye to drain aqueous humor from the anterior chamber into the circular space formed by the plate and, from there, into the subconjunctival space. Molteno also discloses in U.S. Pat. No. 4,457,757 a pair of plates to increase the surface area required for proper drainage of aqueous humor.

The Molteno implant presents a number of problems. This implant is comprised of a large, rigid, flat plate which is not designed to fit on the globe of the eye given that the globe is spherical and the implant is flat. The Molteno implant has a tendency to stretch and tear fragile conjunctival mucous membranes because of its rigidity and lack of contoured shape. Also, the Molteno device requires a minimum of two sutures anteriorly at positions designated 10 and 20 of the Molteno patents and, therefore, the posterior aspect of the plate has a tendency to be excessively mobile after implantation.

Additionally, the Molteno device comes in single and double plate variations. The single plate device seems to work reasonably well early, but fails late in a high percentage, approximately fifty percent, of patients. The second generation double plate device avails a larger surface area for drainage. Unfortunately, it is much more difficult to install surgically than the single plate, requiring multiple (at least four) sutures to implant, thereby complicating the surgery given that each suture pass potentially dangerous. Furthermore, the surgeon installing the double plate is required to open up the entire superior 200 degrees of the eye in order to install it properly. Also, the tube which connects the two plates was intended initially to pass underneath the superior rectus muscle, but this is technically impossible in most cases and therefore a plastic tube is allowed to rest exterior to the superior rectus muscle and is at risk for extrusion.

Compared to the single plate, the double plate Molteno implant has a lower rate of late failure, approximately twenty-five percent. However, recent literature shows that both Molteno devices restrict ocular movement and cause double vision in patients because of their rigidity and size. The implant essentially traps the extraocular muscles which move the eye and creates blocks to the smooth excursion of the globe, thereby causing misalignment of the eyes and double vision.

Although the Molteno implants have been one of the most commercially successful of all glaucoma drainage devices, the problems with the Molteno implants are significant. The Molteno implant utilizes an implant design which essentially is not biocompatible with its implant environment and which tends to result in multiple complications associated with its implantation. This requires multiple modifications by the surgeon in implantation, thus making it difficult to employ. It requires the most highly skilled ophthalmic surgeons to utilize it effectively, and even then presents significant problems. Finally, the tube of this device, and all others which do not restrict access of flow of fluid early in the postoperative period, results frequently in early hypotony or exceedingly low intraocular pressures which induces significant early postoperative complications. Surgeons have modified the device by ligating the silastic tubing which connects the anterior chamber to the plate with a rapidly dissolving suture material to try to blunt this adverse effect. The amount of pressure required for the ligature is thereby left to the technical skills of each individual surgeon and therefore produces erratic results with regard to early pressure reduction in patients implanted with this device.

Other glaucoma implant devices have been utilized to drain aqueous humor from the anterior chamber of the eye to reduce intraocular pressure. For example, Shocket discloses in U.S. Pat. Nos. 4,826,478 and 4,722,724 an implant device and surgical technique for treating neovascular glaucoma using an anterior chamber tube shunt and a silicone band which is positioned to encircle the globe of the eye. According to Shocket, the silastic tube is cradled on the silicone band, with one end of the tube positioned into the anterior chamber.

The Shocket device and procedure present a number of problems. First, the device must be assembled by the surgeon prior to the procedure, which process is extremely labor-intensive. The device is not manufactured in its appropriate configuration and this leads to considerable inherent variations in the device as implanted. Second, the implantation of the device requires dissection of the entire circumference of the globe and disruption of structures which ultimately need not be manipulated in order to implant a device which would create a posterior reservoir for the drainage of aqueous humor. Third, the Shocket procedure requires multiple sutures in all quadrants of the globe in order to firmly attach the silicone band to the sclera. Fourth, the device requires ligation of the silastic band to prevent early post-operative hypotony by the surgeon at the time of the procedure. Fifth, the Schocket procedure is designated a multiple piece device which in recent studies have been found to be less successful in the management of intractable glaucoma than single piece devices such as the present invention. See Lavin, Franks, Wormlawd and Hitchings, *Archives of Opthalmoloqy*, Volume 110, April 1992, pages 480-485.

Others have disclosed various devices and procedures for treating glaucoma through implants that drain aqueous humor. Many of these efforts have been attempted to address the problems of hypotony, fibrosis and other complications caused by implanting glaucoma drainage devices. These include Krupin on valve implants and filtering surgery, *American Journal of Opthalmology*, Volume 81, No. 2, pages 232-235 (1976); Donowitz, U.S. Pat. No. 3,788,327; and Haas, U.S. Pat. No. 4,402,681. The Krupin article discloses numerous attempts at solving the problems associated with permanent seton installation requirements, such as friction between the eyelids, extraocular muscles and other ocular adnea with the device, overly complicated construction and overly difficult surgical implantation techniques, as well as problems with frequent need for additional post-operative invasive surgical procedures to address post-operative complications. However, the Krupin device and all others with valves in the tube which connect the plate with the anterior chamber are routinely associated with obstruction of the valve by fibroblasts which render the device useless because of an unapproachable obstruction to aqueous flow out of the eye.

A number of other devices and related surgical procedures designed by Krupin, White, and others exist for the drainage of aqueous humor to reduce intraocular pressure as a means of treating glaucoma. All of these disclose a tube or shunt for draining aqueous humor from the anterior chamber of the eye. Many current devices require the surgeon to place an external suture on the silastic tube to prevent early post-operative hypotony, or the procedure is divided into two stages to prevent the problem of early post-operative low intraocular pressure.

A number of these devices also disclose valves for controlling drainage or for preventing backflow. In the U.S. Pat. No. 4,554,918 to White, for example, an intraocular pressure relief device is disclosed which describes the use of a conduit to drain aqueous humor from the anterior chamber, a reservoir for holding fluid, thereby drained, and a check valve to prevent backflow. The problem with this device is that the reservoir is emptied by manual manipulation, which is both inefficient and uncomfortable for the patient. It also increases significant potential risk of extrusion due to frequent manipulation and has therefore been discarded by all but a few surgeons.

Similarly, U.S. Pat. No. 4,729,761 discloses a glaucoma implant device that also relies on the patient to pump aqueous out of a drainage reservoir. Patient manipulation, as delineated above, is uncomfortable, inefficient and increases potential for extrusion as well as breakdown of surrounding tissue which can present catastrophic complications, such as endophthalmitis, associated with the use of the devices.

Additionally, the valves which are placed in the silastic tubing of these other implant devices to prevent hypotony in the early peri-operative period are almost universally fibrosed by pleuripotential macrophages. These are cells which are found in the anterior chamber of the eye. After surgery, these cells drain through the tube shunt, attach to the valve and, through a process of fibrosis, obstruct the tube at the site of the valve thereby making the device inoperative.

The present invention improves upon the prior art of glaucoma implant devices. One object of the present invention is to provide an implant device and related surgical procedure for treating glaucoma by reducing intraocular pressure on a regular basis without significant post-operative complications and which also will result in long-term successful shunting of fluid from the anterior chamber into the orbit of the eye.

Another object of the invention is to provide a glaucoma implant device which is biocompatible with the human eye, both through the materials used in the structure of the device and through its shape following the natural contours of the eye and ocular adnea.

Another object of the present invention is to provide an implant device and related surgical procedure for treating glaucoma using a device which is quickly adapted to varying eye sizes of patients, which does not require extensive surgeon time either before surgery to customize each implant to fit a patient to be operated upon, during surgery through extensive incision, suturing, placement or other surgical procedures required to implant the device, or after implantation by requiring additional corrective surgery or other labor intensive monitoring of the implant.

Another object of the invention is to provide a glaucoma implant device and related surgical procedure whereby installation of the device involves a minimal interruption of normal tissues and, preferably, disturbs only one quadrant of the globe.

Yet another object of the invention is to provide a glaucoma implant device which is accessible and ready for implantation as a pre-manufactured, single-piece device to facilitate uniform quality of the device before surgery, to ensure that the device is uniform for any successive surgical procedure, and to facilitate its implantation, thereby eliminating the requirement that the device be used only by the most highly skilled surgeons.

Still another object of the present invention is to provide a glaucoma implant device having a pre-placed ligature to prevent early post-operative hypotony.

Another object of the invention is to provide a glaucoma implant device which is free of any valves which present opportunities for obstruction of the tube shunt by the natural healing mechanisms available to the body, such as pleuripotential macrophages.

Yet another object of the invention is to provide an implant device and related surgical procedure for treating glaucoma whereby complications of glaucoma implant surgery are minimized using design features of the implant, which features are quickly implemented by the surgeon with minimal discomfort or risk of complication to the patient, including but not limited to making the device of a flexible, biocompatible material, markings placed on the tube shunt to facilitate precise and accurate placement of the tube within the anterior chamber of the eye, and minimal suturing of the device onto the sclera while still achieving stable implantation through special design features of the device.

Another object of the invention is to provide a glaucoma implant device of sufficient surface area to supply an adequate cavity for reception of aqueous humor and thereby allow appropriate diffusion of the fluid from the anterior chamber into the orbital tissues.

BRIEF SUMMARY OF THE INVENTION

The present invention is comprised of a lightweight, flexible, biocompatible device, and related surgical procedure, which can be implanted easily and quickly by a surgeon, is comfortable for the patient to live with after implantation without restricting eye movement or requiring manual manipulation, and minimizes complications caused by hypotony, fibrosis or other incidences of surgery during and after implantation of the device. The invention is comprised of a curvilinear band which is flexible to conform to the surface of the eye, the sclera. The band has a main reservoir and, in the preferred embodiment, two smoothly rounded and beveled wings extended opposite each other from the main reservoir to facilitate stabilization of the device by placement of the wings under the extraocular muscles of the eye. The band is connected to a drainage tube which is passed through an incision into the anterior chamber of theleye. The drainage tube of the present invention is further defined by indicia for correctly sizing and placing it within the anterior eye chamber of the eye of each respective patient.

The band is further defined by peripheral baffling formed around the entire perimeter which forms the reservoir to optimize surface area and flow of fluid into a fibrovascular sheath that develops after surgical implantation. Interior baffling formed within the peripheral baffling further directs the flow of aqueous in appropriate paths within the main reservoir. A plurality of full thickness fenestrations spaced around and in the main reservoir of the band facilitate fibrosis between tenon's capsule and the sclera and, if necessary, additional suture sites, and thereby further enhance implant stability.

The present invention is further defined by a tab integrally formed at a midpoint edge of the band between the wings. The tab is used to suture the present invention onto the sclera with a single suture. The drainage tube passes over the tab and extends from a tube bore formed at the midpoint edge of the band over the tab. A dissolvable tube clamp compresses the drainage tube closed, thereby pre-crimping it at the time of implantation to restrict the flow of aqueous humor and to prevent early post-operative excessive filtration with its attending morbidity. The clamp dissolves in two to three weeks following implantation, allowing gradual reduction of resistance to aqueous outflow, or may by lysed earlier if so desired by the surgeon using, for example, a laser to sever the clamp. In the preferred embodiment, the tube clamp is a dark colored pigment to aid in early severance.

The implant device of the present invention is surgically implanted generally by utilizing the procedure comprised of the steps of marking a suture site point on the sclera, entering the anterior chamber to create a paracentesis to accomodate the drainage tubing, placing the device onto the chosen globe quadrant and securing the beveled wings underneath the superior and lateral or medial rectus muscles, bringing the tab into position over the marked suture site and then suturing the tab to the sclera to secure the implant in place. The drainage tube then is trimmed for patient fit and placed into the anterior chamber through the paracentesis.

In the preferred surgical procedure embodiment of the present invention, a partial thickness scleral flap of 3-4 mm in size may be elevated before creating the paracentesis to help protect the overlying conjunctiva from eroding the silastic tube and to smooth the path of the silastic tube into the anterior chamber. Additionally, before implantation, an antifibroblastic agent is placed on Weck Cell sponges which are placed on the sclera and in the subtenon's space for a short period of time. The sponges then are removed and the area is irrigated with copious amounts of balanced salt solution. Implantation follows as detailed above. Then, before placement of the drainage tube, a viscolastic agent is injected into the anterior chamber through the paracentesis site to ensure full depth access of the anterior chamber.

BRIEF DESCRIPTION OF THE DRAWINGS

A fuller understanding of the foregoing may be derived by reference to the accompanying drawings, wherein:

FIG. 4 is a side elevational view of a human eye upon which the device of the present invention has been implanted.

FIG. 5 is a partial perspective view of the main reservoir, peripheral baffling, interior baffling and fenestrations, suturing tab, clamp and drainage tube and one of the beveled band wings.

FIG. 6 is a close-up, partial side elevational view of one of the beveled band wings of the present invention stabilized under the extraocular muscles to secure the present invention in place upon implantation.

FIG. 7 is a bottom plan view of the present invention.

DETAILED DESCRIPTION OF THE INVENTION

The objects of the present invention, its advantages and other aspects will be apparent upon consideration of the following detailed description of the invention. This detailed description is intended to disclose the invention by way of example through preferred embodiments, and is not intended to limit the spirit and scope of the invention.

Figure 1:
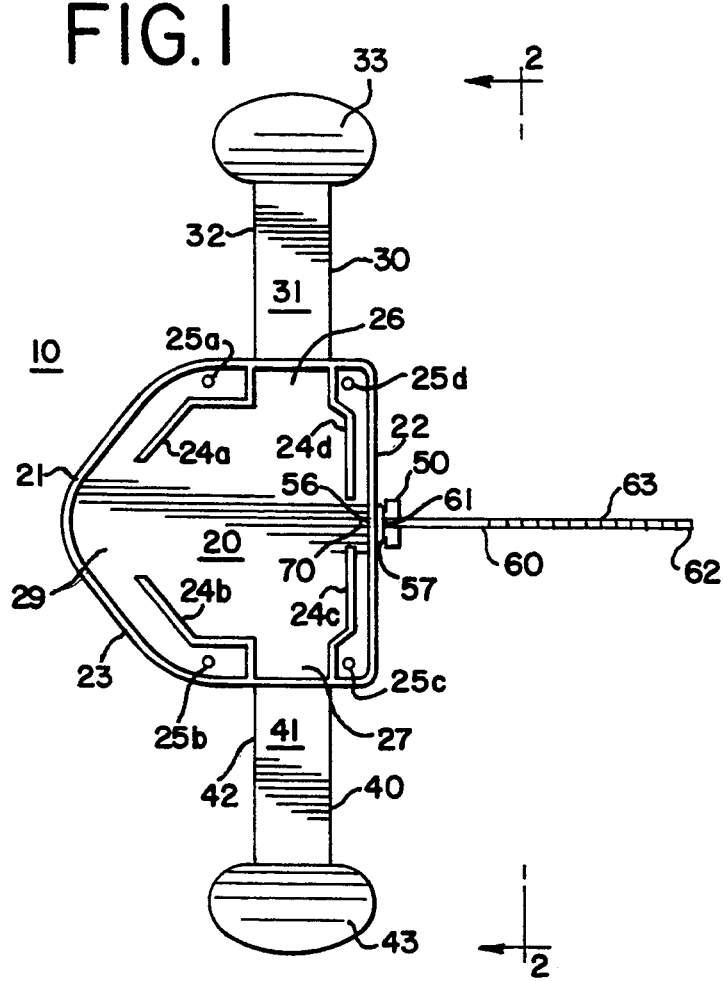
FIG. 1 is a top plan view of the present invention showing the main reservoir, beveled wings, tab, drainage tube with placement indicia and tube clamp.

Referring now to FIG. 1, the glaucoma implant device 10 as shown forms a band made of a durable, flexible, biocompatible material such as silicone, said band having a main reservoir 20. Said reservoir 20 is further defined by a posterior end 21, an anterior end 22, and peripheral baffling 23 formed around the perimeter of said main reservoir 20. Said main reservoir 20 is further defined by interior baffling 24a, 24b, 24c and 24d for directing fluid flow within said main reservoir 20, as well as fenestrations 25a, 25b, 25c, and 25d for generating columns of fibrous tissue between the sclera and the tenon's capsule to assist in anchoring and stabilizing the implant in place. Fenestrations 25 a-d also may be used, if necessary, as additional suture sites for further stabilizing the implant. Interior baffling 24a and 24b extend from said peripheral baffling 23 around said fenestrations 25a and 25b, respectively, the main body of said interior baffling 24a and 24b being generally parallel to said peripheral baffling 23 at posterior end 21 and formed to control flow of fluid from said fenestrations 25a and 25b into said main reservoir 20. Interior baffling 24c and 24d extend from said peripheral baffling 23 around said fenestrations 25c and 25d, respectively, the main body of said interior baffling 24c and 24d being generally parallel to said peripheral baffling 23 at anterior end 22 and formed to control flow of fluid from said fenestrations 25c and 25d into said main reservoir 20. Additionally, said interior baffling 24a, 24b, 24c, and 24d creates a permanent elevated space to hold and distribute aqueous humor into the orbital subconjunctival space for absorption by surrounding tissues.

As shown in FIG. 1, the device 10 is further defined by said main reservoir 20 having a first band end 26 from which a first beveled band wing 30 extends, and a second band end 27 from which a second beveled band wing 40 extends in opposite direction from beveled band wing 30, said beveled band wings 30 and 40 being disposed generally in linear alignment with one another. Each beveled wing 30 and 40 has a neck portion 31 and 41, respectively, an end depression 32 and 42, respectively, and an anchoring head 33 and 43, respectively. Additionally, the device 10 has a bottom surface 28 which contacts the sclera of the eye and a top surface 29 from which a fibrovascular drainage sheath develops after implantation to allow for drainage of aqueous fluid from the anterior chamber into the subconjunctival space.

FIG. 1 also shows tab 50 integrally formed to the main reservoir 20 at anterior end 22. In the preferred embodiment of the invention, tab 50 is formed midway between said first band end 26 and said second band end 27 along anterior end 22 of main reservoir 20 at midpoint 70. Drainage tube 60 is shown affixed to the device 10 over tab 50, with drainage tube 60 formed of a flexible, biocompatible material such as a silastic tube, said drainage tube 60 being further defined by a reservoir end 61, an anterior chamber end 62 and tube placement markings 63. At midpoint 70 above tab 50, tube bore 56 is integrally formed in said peripheral baffling 23 of main reservoir 20, from which tube bore 56 depends drainage tube 60 from said reservoir end 61.

Figure 2:
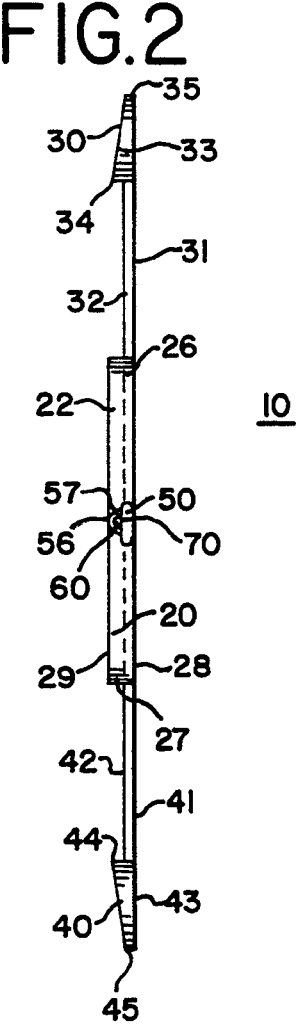
FIG. 2 is a side elevational view of the present invention taken along line 2—2 of FIG. 1 in a flat configuration.

FIG. 2 shows the preferred embodiment of the invention depicted in FIG. 1 from a side elevational view of said anterior end 22 of the device 10, absent said drainage tube 60. FIG. 2 shows more clearly the depressions 32 and 42 of beveled wings 30 and 40, respectively. In the preferred embodiment of the invention, said depressions 32 and 42 are formed along the top surface 29 of the device 10 for the length of neck portion 31 and neck portion 41, respectively, ending at said main reservoir 20 and anchoring heads 33 and 43, respectively. Also in the preferred embodiment of the invention, as shown in FIG. 2, anchoring ends 33 and 43 are further defined by lock ends 34 and 44, respectively, and tip ends 35 and 45, respectively. Tip ends 35 and 45 are tapered to facilitate guided placement of beveled band wings 30 and 40 under the extraocular muscles of the eye. Anchor ends 33 and 43 gradually increase in thickness from said tip ends 35 and 45 to said lock ends 34 and 44 to help form depressions 32 and 42, respectively, thereby providing the locking contouring of the beveled wings 30 and 40 which helps stabilize the device 10 upon implantation, as also shown in partial close-up view for wing 41 in FIG. 6. Additionally, FIG. 2 shows tube bore 56 integrally formed at said anterior end 22 of the main reservoir 20 above said tab 50 at midpoint 70, and to which said reservoir end 61 of said drainage tube 60 is secured to flow aqueous humor from the anterior chamber of the eye where said anterior chamber end 62 of said drainage tube 60 is placed, and into said main reservoir 20 for drainage.

Figure 3:
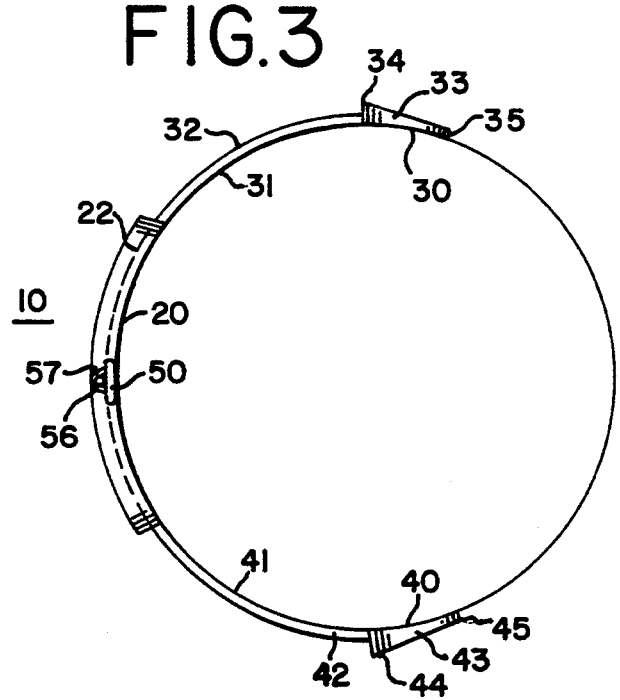
FIG. 3 is a side elevational view of the present invention taken along line 2—2 of FIG. 1, showing the curvilinear formation of the device as implanted.

FIG. 3 shows a side elevational view of the device 10 in its curvilinear form as implanted on a human eye. FIGS. 4 and 5 further show the device 10 as implanted on a human eye. In the preferred embodiment of the invention, as shown in FIGS. 4 and 5, bottom surface 28 of the device 10 is placed on the sclera of an eye, with said posterior end 21 directed generally toward the posterior of the patient's eye, and said anterior end 22 directed generally toward the lens of the eye. Said beveled wings 30 and 40 are placed under the extraocular muscles of the eye. The drainage tube 60, measured and cut to desired length using tube markings 63, is inserted through incision site 58 of the eye into the anterior chamber. The device 10 then is stabilized on the sclera by a single suture through tab 50 at suture site 55.

FIG. 5 shows a close-up, partial perspective view of the main reservoir 20 from anterior end 22, showing in particular tab 50 and said drainage tube 60 depended from the main reservoir 20 over said tab 50. Tube clamp 57 clamps the tube 60 at said reservoir end 61 to temporarily restrict the flow of aqueous from the anterior chamber upon implantation, thereby preventing early post-operative excessive filtration and consequent hypotony.

In the preferred embodiment of the invention, the implant device 10 is comprised of a curvilinear band approximately 33 mm long from said tip end 35 to said tip end 45, by 16 mm wide from said anterior end 22 to the midrange of said posterior end 21, said posterior end 21 being bowed in the preferred embodiment of the invention to facilitate placement of the device 10 on the eye while at the same time maximizing reservoir surface area. Posterior end 21, however, may take various configurations in alternative embodiments while achieving these same objectives. The drainage tube 60 is approximately 0.64 mm in external diameter and approximately 30 mm long, with said tube markings 63 designated at 2 mm intervals on said tube 60. Also in the preferred embodiment of the invention, tube clamp 57 is formed of 7.0 polyglycolate and darkened in pigment, such that it naturally dissolves in a period of two to three weeks to gradually allow flow of aqueous into said main reservoir 20. Alternatively, tube clamp 57 can be lysed by, for example, laser if needed earlier by the surgeon, which lysing is facilitated by the dark pigment of said tube clamp 57, to allow for fluid flow sooner.

To prepare for surgical implantation of the preferred embodiment of the device 10, the patient is appropriately anesthetized and prepared for surgery through placement of a broad based lid speculum. A suture, preferably a 4-0 silk suture, is passed underneath each of the superior rectus muscles. An incision then is made in the conjunctiva at approximately 7-8 mm posterior to the limbus in the superotemporal quadrant. This incision then is taken down to the sclera and extended over the superior and lateral rectus muscles. A conjunctival flap then is generated with a base at the limbus using blunt and/or sharp dissection, followed by bipolar cautery to achieve homeostasis. Muscle hooks passed underneath the rectus muscles are used if necessary to aid in controlling the muscles for the final placement of the silk sutures.

To optimize visualization of the superotemporal or superotemporal quadrant and areas around each of the muscles, excessive tenon's capsule or conjunctival fibrotic tissue dissected away from the muscles and sclera. Suture site 55, shown in FIG. 5, then is marked using calipers to designate a point approximately equidistant between the superior and lateral or medial rectus muscles, approximately 7 mm posterior to the limbus. A tab suture 54, shown in FIG. 5, preferably a 5-0 Mersilene suture, is passed with the scleral pass encompassing approximately 3 mm of sclera. Said suture 54 then is draped anteriorly, and the conjunctival flap is checked to insure dissection up to the limbus. A paracentesis then is formed at incision site 58, shown also in FIG. 5, preferably using a super sharp 15 degree angular blade, to enter the anterior chamber. At this point a partial thickness scleral flap 3-4 mm square may be elevated by dissection to facilitate a more gentle entry into the anterior chamber and to help to protect the overlying conjunctive from erosion of the drainage tube 60.

After irrigating the field liberally with balanced salt solution, the device 10 then is positioned on the scleral surface of the superotemporal quadrant with posterior end 21 generally directed posteriorly. Tip ends 35 and 45 of beveled band wings 30 and 40, respectively, are used to guide wings 30 and 40 underneath the superior and lateral rectus muscles until anchoring head 33 and 43 of wings 30 and 40, respectively, have passed underneath these muscles to allow the superior and lateral or medial rectus muscles to rest directly on wing depressions 32 and 42 of necks 31 and 41 of wings 30 and 40, respectively. Locking ends 34 and 44 of anchoring heads 33 and 43, respectively, further serve to stabilize the wings 30 and 40 against the superior and lateral or medial rectus muscles, as shown in FIG. 4 and 5. Tab 50 then is brought into position over marked suture site 55. Said tab suture 54 then is cut and tied around tab 50 to secure the device 10 in place. If further suturing stabilization is needed, fenestrations 25a-d may serve as additional suture sites.

Subsequently, said drainage tube 60 is sized utilizing said tube markings 63 to effect approximately 2-3 mm of said drainage tube 60 abutting into the anterior chamber, anterior to the surface of the iris. After trimming said drainage tube 60 to the desired length, anterior chamber end 62 is inserted through incision side 58 for placement of said tube 60 within the anterior chamber as detailed above.

Homeostasis then is checked and, once achieved, the muscle hooks and sutures placed to control the superior and lateral rectus are removed. Tenon's capsule and the conjunctiva then are sutured closed, preferably using a 7-0 to 9-0 Vicryl suture. The patient then may receive subconjunctival injections of antibiotics and/or steroids, with the eye then being patched with appropriate antibiotic and/or steroidal ointments, as well as standard protective coverings.

In an alternate preferred embodiment of the surgical procedure for implanting the device 10, antifibroblastic agents are employed, such as Mitomycin C, 0.4-0.5 mg/ml, to discourage occlusion of the anterior chamber end 62 of the drainage tube 60 after placement within the anterior chamber. Prior to introduction of the device 10 to the field, antifibroblastic agents are directed beneath the anterior and posterior lips of the conjunctival flaps, preferably using as applicators Weck cell sponges impregnated with antifibroblastic agents. The antifibroblastic agents remain as applied for a short period of time, preferably two to five minutes. After this time, antifibroblastic agent applicators, such as the Weck cell sponges, are removed and the area is irrigated with copious amounts of balanced salt solution. Other medications such as those commercially sold as "Bleomycin" "Methotrexate" or "Adnomycin" may be substituted for Mitomycin C. The device 10 is implanted as detailed above, but before insertion of drainage tube 60 into the anterior chamber, a viscolastic agent, such as those sold commercially under the names "Healon", "Viscoat", "Amvise" or "Occucoat" is injected into the anterior chamber through incision site 58 to ensure full depth access of the anterior chamber. The remainder of the surgical procedure follows the description detailed above.

As a result of implantation utilizing the present invention and related surgical procedure, a fibrovascular sheath forms over the main reservoir 20 from top surface 29 and aided by interior baffling 24a, 24b, 24c, and 24d. Fibrosis generates columns at fenestrations 25a, 25b, 25c and 25d to stabilize implantation of the device 10 by anchoring said main reservoir 20 at bottom surface 28 between the sclera and tenon's capsule. After formation of this sheath, which takes approximately one to two weeks, tube clamp 57 either has dissolved naturally or been lysed by the surgeon, thereby allowing for flow of aqueous from the anterior chamber, through drainage tube 60, through tube bore 56 over tab 50 and into said main reservoir 20. Aqueous humor diffuses from said main reservoir 20 beyond the fibrovascular sheath and into the subconjunctival space.

What I claim is:

1. A device to be surgically implanted in an eye for treating glaucoma by draining aqueous humor out of the anterior chamber of the eye, said device comprising:

a main reservoir having a base surface, a tube end, a flexible tube depended from said tube end and adapted to be shunted to the anterior chamber for draining fluid therefrom and into said main reservoir, and;

stabilization means comprised of a plurality of wings extended away from said main reservoir and adapted to cooperatively associate with the extraocular muscles of the eye, said wings each having an elongated neck portion and an anchoring head enlarged relative to said neck portion to allow for releasable locking engagement with the extraocular muscles.

2. The device recited in claim 1, wherein said stabilization means is further defined by a suture site tab formed integrally on said main reservoir at said tube end and adapted to receive a suture for securing said device to the sclera.

3. The device recited in claim 1, wherein:

said tube is further defined by size adjustment guide means comprised of a plurality of exterior circumferential markings regularly placed on said tube for assisting in modification of the size of said tube.

4. The device recited in claim 1, wherein:

said wings are further defined by a depression formed on said neck portion and said anchoring head each having a tip end and a lock end, with each said anchoring head gradually increasing in thickness to form a taper from each said tip end to each respective lock end.

5. The device recited in claim 4, wherein said stabilization means is further defined by a plurality of fenestrations formed through said base surface of said main reservoir for anchoring said band t the sclera by fibrosis.

6. The device recited in claim 4, wherein said stabilization means is further defined by a plurality of fenestrations formed through said base surface of said main reservoir for anchoring said band to the sclera by fibrosis and having a suture site tab formed integrally on said tube end of said main reservoir and adapted to receive a suture for securing said device to the sclera.

7. A device to be surgically implanted for treating refractory glaucoma by draining aqueous humor out of the anterior chamber of an eye, said device comprising:

a band formed of material biocompatible with the eye surface and ocular adnea, said band having a main reservoir with a base surface, a tube end and a tube bore formed at said tube end, said band further defined by a flexible tubular shunt depended from said main reservoir in cooperative coaxial association with said tube bore;

stabilization means integrally associated with said band for securing said device into implanatation position;

size guide means for assisting in adaption of said implant to variously sized eyes;

flow control means for controlling the flow of aqueous from the anterior chamber.

8. The device recited in claim 7, wherein said stabilization means is comprised of a plurality of wings extended away from said main reservoir, said wings each having a neck portion and an anchoring head.

9. The device recited in claim 8, wherein said stabilization means is further defined by a suture site tab formed integrally at said tube end of said main reservoir under said tube bore and adapted to receive a suture for further securing said device to the sclera.

10. The device recited in claim 7, wherein:

said stabilization mean sis comprised of a plurality of wings extended away from said main reservoir, said wings each having a neck portion and an anchoring head.

said size guide means is comprised of a plurality of exterior circumferential markings regularly placed on said tubular shunt.

11. The device recited in claim 7, wherein:

said stabilization means is comprised of a plurality of wings extended away from said main reservoir, said wings each having a neck portion defining a depression in said wing and an anchoring head each having a tip end and a lock end, with each said anchoring head gradually increasing in thickness to form a taper from each said tip end to each respective lock end, and a plurality of fenestrations formed through said base surface of said main reservoir for anchoring said band to the sclera by fibrosis;

said size guide means is comprised of a plurality of exterior circumferential markings regularly placed on said tubular shunt.

12. The device recited in claim 7, wherein:

said stabilization means is comprised of a plurality of wings extended away from said main reservoir, said wings each having a neck portion defining a depression in said wing and an anchoring head each having a tip end and a lock end, with each said anchoring head gradually increasing in thickness to form a taper from each said ti end to each respective lock end, said stabilization means further comprised of a suture site tab formed integrally at said tube end of said main reservoir under said tube bore and adapted to receive a suture for further securing said device to the sclera, said stabilization means further comprised of a plurality of fenestrations formed through said main reservoir for anchoring said band to the sclera;

said size guide means is comprised of a plurality of exterior circumferential markings regularly placed on said tubular shunt.

13. The device recited in claim 7, wherein said flow control means is comprised of a ligature formed of a gradually dissolvable material.

14. The device recited in claim 13, wherein said ligature is formed of a colored pigment to be located readily for early release by severing said ligature before natural dissolution.

15. The device recited in claim 7, wherein said flow control means is comprised of interior baffling formed within said main reservoir.

16. The device recited in claim 7, wherein said flow control means is comprised of interior baffling formed within said main reservoir to hold and distribute aqueous humor drained into said main reservoir for absorption into the subconjunctival space and surrounding tissue, said flow control means being further defined by a ligature formed of a gradually dissolvable material and a colored pigment.

17. The device recited in claim 7, wherein:
said stabilization means is comprised of a plurality of wings extended away from said main reservoir, said wings each having a neck portion defining a depression in said wing and an anchoring head each having a tip end and a lock end, with each said anchoring head gradually increasing in thickness to form a taper from each said tip end to each respective lock end, said stabilization means being further comprised of a suture site tab formed integrally at said tube end of said main reservoir and adapted to receive a suture for further securing said device to the sclera, said stabilization means being further comprised of a plurality of fenestrations formed through said base surface of said main reservoir for anchoring said band to the sclera by fibrosis;
said size guide means is comprised of a plurality of exterior circumferential markings regularly placed on said tubular shunt; and
said flow control means is comprised of interior baffling formed within said main reservoir, and a ligature formed to crimp said tubular shunt upon implantation, said ligature being comprised of a gradually dissolvable material formed of a colored pigment.

18. A pre-assembled, flexible implant device to be surgically implanted in an eye for treating refractory glaucoma by draining aqueous humor out of the anterior chamber of the eye using a shunt, said device comprising:
a band having a main reservoir with a base surface, a tube end, and a tube bore formed at said tube end, said band further defined by a tubular shunt depended from said main reservoir in cooperative coaxial association with said tube bore;
stabilization means integrally associated with said band for securing said device into implantation position;
size guide means for assisting in adaptation of said implant to variously sized eyes; and
flow control means for controlling the flow of aqueous humor from the anterior chamber.

19. The device recited in claim 18, wherein:
said band is formed of material biocompatible with the eye surface and ocular adnea;
said stabilization means is comprised of a plurality of wings extended away from said main reservoir, said wings each having a neck portion and an anchoring head.

20. The device recited in claim 18, wherein said band is formed of silicone.

21. The device recited in claim 18, wherein:
said band is formed of material biocompatible with the eye surface and ocular adnea;
said stabilization means is comprised of a plurality of wings extended away from said main reservoir, said wings each having a neck portion and an anchoring head, said stabilization means being further defined by a suture site tab formed integrally on said main reservoir at said tube end and adapted to receive a suture for further securing said device to the sclera.

22. The device recited in claim 18, wherein:
said band is formed of material biocompatible with the eye surface and ocular adnea;
said stabilization means is comprised of a plurality of wings extended away from said main reservoir, said wings each having a neck portion and an anchoring head;
said size guide means is comprised of a plurality of exterior circumferential markings regularly placed on said tubular shunt.

23. The device recited in claim 18, wherein:
said band is formed of material biocompatible with the eye surface and ocular adnea;
said stabilization means is comprised of a plurality of wings extended away from said main reservoir, said wings each having a neck portion defining a depression is said wing and an anchoring head each having a tip end and a lock end, with each said anchoring head gradually increasing in thickness to form a taper from each said tip end to each respective lock end;
said size guide means is comprised of a plurality of exterior circumferential markings regularly placed on said tubular shunt.

24. The device recited in claim 18, wherein:
said band is formed of material biocompatible with the eye surface and ocular adnea;
said stabilization means is comprised of a plurality of wings extended away from said main reservoir, said wings each having a neck portion defining a depression is said wing and an anchoring head each having a tip end and a lock end, with each said anchoring head gradually increasing in thickness to form a taper from each said tip end to each respective lock end, said stabilization means being further comprised of a plurality of fenestrations formed through said base surface of said main reservoir for anchoring said band to the sclera by fibrosis;
said size guide means is comprised of a plurality of exterior circumferential markings regularly placed on said tubular shunt.

25. The device recited in claim 18, wherein:
said band is formed of material biocompatible with the eye surface and ocular adnea;
said stabilization means is comprised of a plurality of wings extended away from said main reservoir, said wings each having a neck portion defining a depression in said wing and an anchoring head each having a tip end and a lock end, with each said anchoring head gradually increasing in thickness to form a taper from each said tip end to each respective lock end, said stabilization means being further comprised of a suture site tab formed integrally on said main reservoir at said tube end and adapted to receive a suture for securing said device to the sclera, said stabilization means being still further comprised of a plurality of fenestrations formed through said main reservoir for anchoring said band to the sclera by fibrosis;
said size guide means is comprised of a plurality of exterior circumferential markings regularly placed on said tubular shunt.

26. The device recited in claim 18, wherein said flow control means is comprised of a ligature formed of a gradually dissolvable material.

27. The device recited in claim 26, wherein said ligature is formed of a colored pigment.

28. The device recited in claim 18, wherein said flow control means is comprised of interior baffling formed within said main reservoir.

29. The device recited in claim 18, wherein said flow control means is comprised of interior baffling formed within said main reservoir and a ligature affixed to said device in position to crimp said tubular shunt near said main reservoir to prevent fluid flow at implantation, said ligature being formed of gradually dissolvable material and a colored pigment.

30. The device recited in claim 18, wherein:
said band is formed of material biocompatible with the eye surface and ocular adnea;
said stabilization means is comprised of a plurality of wings extended away from said main reservoir, said wings each having a neck portion defining a depression in said wing and an anchoring head each having a tip end and a lock end, with each said anchoring head gradually increasing in thickness to form a taper from each said tip end to each respective lock end;
said size guide means is comprised of a plurality of exterior circumferential markings regularly placed on said tubular shunt,
said flow control means is comprised of interior baffling formed within said main reservoir and a ligature affixed to said device in position to crimp said tubular shunt near said main reservoir to prevent fluid flow at implantation, said ligature being formed of a gradually dissolvable material and a colored pigment.

31. A pre-assembled, flexible implant device to be surgically implanted for treating refractory glaucoma by draining aqueous out of the anterior chamber of an eye, said device comprising:
a band having a main reservoir having a tube end, external baffling, a bottom wall, and a tube bore formed at said tube end, said band further defined by a tubular shunt depended from said main reservoir in cooperative coaxial association with said tube bore, said band further defined by at least two wings extended away from said main reservoir in opposite directions relative to one another, said wings each having a neck portion and an anchoring head, said neck portion forming a depression in said wing and each said anchoring head gradually increasing in thickness to with each said anchoring head gradually increasing in thickness to form a taper from each said tip end to each respective lock end to guide each said anchoring head under and past the extraocular muscles of the eye which then lock against each said lock end and rest in said depressions, said band being further defined by a suture site tab integrally formed on said main reservoir outside said exterior baffling and under said tube bore;
a plurality of circumferential markings regularly placed on said tubular shunt to assist in sizing said tubular shunt for placement within the anterior chamber according to the size of the eye;
a ligature integrally formed on the exterior of said main reservoir above said tab to releasably pre-crimp said tubular shunt.

32. The device recited in claim 31, wherein said wings are comprised of two in number, extended in linear alignment away from said main reservoir in opposite directions relative to one another.

33. The device recited in claim 31, wherein said circumferential markings are placed between one to three millimeters apart.

34. A method for treating glaucoma with a surgical implant device formed from a flexible band that is biocompatible with the eye surface and ocular adnea, said band having a main reservoir, a flexible tubular shunt depended from said main reservoir, and stabilization means comprised of a plurality of wings extended away from said main reservoir, said method comprising the steps of:
dissecting a conjunctival flap in the superotemporal eye quadrant;
clearing the implant field;
marking a suture site after clearing the implant field;
passing a suture through the sclera at said suture site;
forming a apracentesis to access the anterior chamber;
securing the device on the eye using said stabilization means as further comprised of a tab integrally formed on said main reservoir between said wings, said step of securing the device being comprised of placing said wings under and past the superior and lateral or medial muscles of the eye, than threading and knotting said pre-placed suture through said tab to stabilize said device in the field;
adapting said tubular shunt by trimming it at one of a plurality of circumferential markings regularly placed on said tubular shunt as eye size adjustment means for sizing said tubular shunt to the appropriate length for correct patient fit in the anterior chamber;
suturing closed the tenon's capsule and the conjunctive.

35. The method recited in claim 34, further defined by directing antifibroblastic agents beneath the anterior and posterior lips of the conjuctival flaps after clearing the implant field but before introducing said device to the field, allowing said antifibroblastic agents to remain as placed for a short period of time, then irrigating the field with copious amounts of balanced salt solution.

36. The method recited in claim 34, further defined by injecting a viscolastic agent into the anterior chamber through the drainage tube incision site before insertion of said drainage tube into the anterior chamber.

* * * * *

UNITED STATES PATENT AND TRADEMARK OFFICE
CERTIFICATE OF CORRECTION

PATENT NO. : 5,370,607
DATED : December 6, 1994
INVENTOR(S) : James E. Memmen

It is certified that error appears in the above-indentified patent and that said Letters Patent is hereby corrected as shown below:

In the drawings, delete Figure 5 and substitute the attached Figure 5 with added reference numeral and lead line —58— illustrated below.

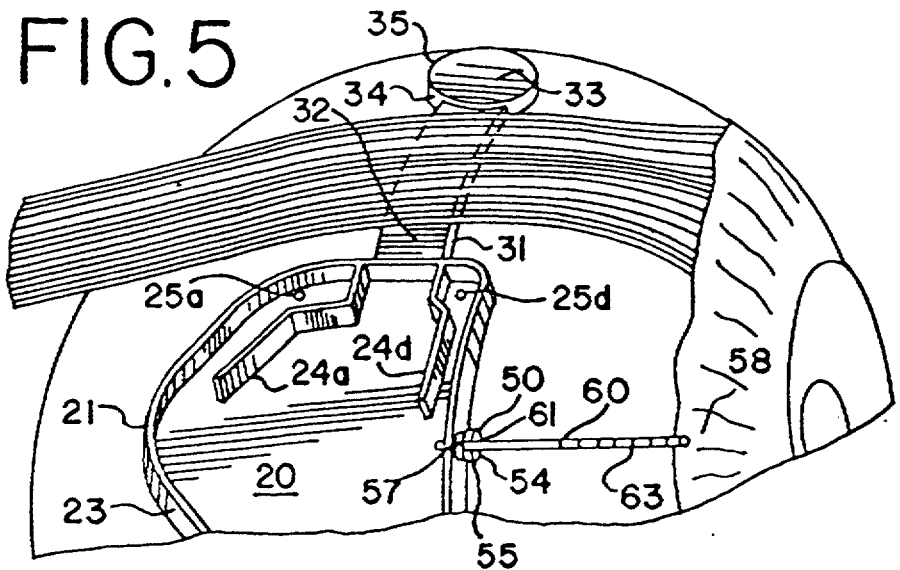

UNITED STATES PATENT AND TRADEMARK OFFICE
CERTIFICATE OF CORRECTION

PATENT NO. : 5,370,607

DATED : December 6, 1994

INVENTOR(S) : James E. Memmen

Page 2 of 2

It is certified that error appears in the above-indentified patent and that said Letters Patent is hereby corrected as shown below:

Column 2, line 51, add —is— after "pass".
Column 6, line 2, change "theleye" to —the eye—.
Column 6, line 31, change "by" to —be—.
Column 7, line 51, change "of-fluid" to —of fluid—.
Column 9, line 54, add —is— after "tissue".
Column 9, line 58, change "mmposterior" to —mm posterior—.
Column 10, line 2, change "junctive" to —juntiva—.
Column 10, line 2, change "frommerosion" to —from erosion—.
Column 11, line 51, change "t the" to —to the—.
Column 12, line 18, change "sis" to —is—.
Column 12, line 47, change "ti" to —tip—.
Column 14, line 19, change "is" to —in—.
Column 15, lines 51-53, delete the phrase "gradually increasing in thickness to with each said anchoring head" and insert —having a tip end and a lock end, with each said anchoring head—.
Column 16, line 30, change "apracentesis" to —paracentesis—.
Column 16, line 37, change "than" to —then—.
Column 16, line 47, change "tive" to —tiva—.

Signed and Sealed this

Eleventh Day of July, 1995

Attest:

BRUCE LEHMAN

Attesting Officer

Commissioner of Patents and Trademarks